(12) United States Patent
Kobayashi et al.

(10) Patent No.: US 10,863,983 B2
(45) Date of Patent: Dec. 15, 2020

(54) MEDICAL STAPLER

(71) Applicant: OLYMPUS CORPORATION, Tokyo (JP)

(72) Inventors: Masayuki Kobayashi, Tokyo (JP); Kayuri Kimura, Saitama (JP); Yoshiyuki Kumada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 172 days.

(21) Appl. No.: 16/180,196

(22) Filed: Nov. 5, 2018

(65) Prior Publication Data

US 2019/0069893 A1    Mar. 7, 2019

Related U.S. Application Data

(63) Continuation of application No. PCT/JP2016/065697, filed on May 27, 2016.

(51) Int. Cl.
*A61B 17/072* (2006.01)
*A61B 17/068* (2006.01)
(Continued)

(52) U.S. Cl.
CPC ...... *A61B 17/0686* (2013.01); *A61B 17/0644* (2013.01); *A61B 17/1155* (2013.01); *A61B 2017/07257* (2013.01)

(58) Field of Classification Search
CPC .......... A61B 2017/07214; A61B 2017/07285; A61B 17/027
(Continued)

(56) References Cited

U.S. PATENT DOCUMENTS 4,289,133 A    9/1981 Rothfuss
4,893,622 A *  1/1990 Green ................. A61B 17/115
                                              227/180.1
(Continued)

FOREIGN PATENT DOCUMENTS

AU    2008207345 A1    3/2009
AU    2010202264 A1    1/2011
(Continued)

OTHER PUBLICATIONS

International Search Report dated Aug. 16, 2016 issued in PCT/JP2016/065697.

*Primary Examiner* — Gloria R Weeks
(74) *Attorney, Agent, or Firm* — Scully, Scott, Murphy & Presser, P.C.

(57) ABSTRACT

A medical stapler according to the present invention is provided with: a staple housing provided with a gripping surface from which a staple for suturing tissue is ejected, and a cutter that cuts the tissue by being made to protrude from the gripping surface; an anvil that is disposed facing a direction in which the staple is ejected, and that is configured so that the tissue can be gripped between the gripping surface and the anvil; and a receiving member that is provided in the anvil, and that has a receiving surface that receives a cutting edge of the cutter, wherein the receiving surface of the receiving member has a shape in which only a portion thereof comes into contact with the cutting edge of the cutter at individual time points during a cutting step over the entire length of a cut length of the tissue.

5 Claims, 6 Drawing Sheets

(51) Int. Cl.
*A61B 17/064* (2006.01)
*A61B 17/115* (2006.01)

(58) Field of Classification Search
USPC ..................................................... 227/180.1
See application file for complete search history.

(56) References Cited

U.S. PATENT DOCUMENTS

| | | | |
|---|---|---|---|
| 6,193,129 | B1 | 2/2001 | Bittner et al. |
| 7,708,180 | B2 * | 5/2010 | Murray ............ A61B 17/00491 |
| | | | 227/175.1 |
| 7,967,181 | B2 | 6/2011 | Viola et al. |
| 8,201,720 | B2 * | 6/2012 | Hessler ............ A61B 17/07292 |
| | | | 227/175.1 |
| 8,464,925 | B2 * | 6/2013 | Hull ................. A61B 17/115 |
| | | | 227/179.1 |
| 9,414,839 | B2 * | 8/2016 | Penna ............... A61B 17/0682 |
| 9,693,773 | B2 * | 7/2017 | Williams ........... A61B 17/1155 |
| 2005/0067460 | A1 * | 3/2005 | Milliman ........... A61B 17/068 |
| | | | 227/180.1 |
| 2010/0065609 | A1 * | 3/2010 | Schwemberger .... A61B 17/115 |
| | | | 227/180.1 |
| 2011/0006102 | A1 | 1/2011 | Kostrzewski |
| 2011/0218562 | A1 | 9/2011 | Viola et al. |
| 2011/0257667 | A1 | 10/2011 | Nakamura et al. |
| 2012/0325892 | A1 | 12/2012 | Kostrzewski |
| 2014/0107676 | A1 | 4/2014 | Kostrzewski |
| 2014/0197225 | A1 | 7/2014 | Penna |
| 2015/0014393 | A1 * | 1/2015 | Milliman ........... A61B 17/1155 |
| | | | 227/180.1 |
| 2015/0060524 | A1 | 3/2015 | Kostrzewski |
| 2016/0157855 | A1 * | 6/2016 | Williams ........... A61B 17/1155 |
| | | | 227/180.1 |
| 2016/0242786 | A1 | 8/2016 | Penna |
| 2017/0181747 | A1 | 6/2017 | Kostrzewski |

FOREIGN PATENT DOCUMENTS

| | | |
|---|---|---|
| AU | 2013270456 A1 | 7/2014 |
| CA | 1156117 A | 11/1983 |
| CA | 2638874 A1 | 2/2009 |
| CA | 2706943 A1 | 1/2011 |
| CA | 2838524 A1 | 7/2014 |
| EP | 2030578 A1 | 3/2009 |
| EP | 2266472 A1 | 12/2010 |
| EP | 2272442 A1 | 1/2011 |
| EP | 2377474 A1 | 10/2011 |
| EP | 2392266 A1 | 12/2011 |
| EP | 2754398 A2 | 7/2014 |
| GB | 2070500 A | 9/1981 |
| JP | S56-132944 A | 10/1981 |
| JP | 2009-056306 A | 3/2009 |
| JP | 2011-015962 A | 1/2011 |
| JP | 2011-224031 A | 11/2011 |
| JP | 2014-133128 A | 7/2014 |

* cited by examiner

MEDICAL STAPLER

CROSS-REFERENCE TO RELATED APPLICATIONS

This is a continuation of International Application PCT/JP2016/065967, with an international filing date of May 27, 2016, which is hereby incorporated by reference herein in its entirety.

TECHNICAL FIELD

The present invention relates to a medical stapler.

BACKGROUND ART

There is a known medical stapler that serves as a treatment tool with which tissue is simultaneously sutured and cut (for example, see Japanese Unexamined Patent Application, Publication No. 2014-133128).

This medical stapler is provided with, inside a pair of jaws that grip the tissue: numerous staples; a mechanism for ejecting the staples; an anvil for deforming the ejected staples; and a cutter with which the tissue sutured with the staples is cut.

SUMMARY OF INVENTION

An aspect of the present invention is a medical stapler including: a staple housing provided with a gripping surface from which a staple for suturing tissue is ejected, and a cutter that cuts the tissue by being made to protrude from the gripping surface; an anvil that is disposed facing a direction in which the staple is ejected, and that is configured so that the tissue can be gripped between the gripping surface and the anvil; and a receiving member that is provided in the anvil, and that has a receiving surface that receives a cutting edge of the cutter, wherein the receiving surface of the receiving member has a shape in which only a portion thereof comes into contact with the cutting edge of the cutter at individual time points during a cutting step over the entire length of a cut length of the tissue.

DESCRIPTION OF EMBODIMENT

A medical stapler 1 according to an embodiment of the present invention will be described below with reference to the drawings.

Figure 1:
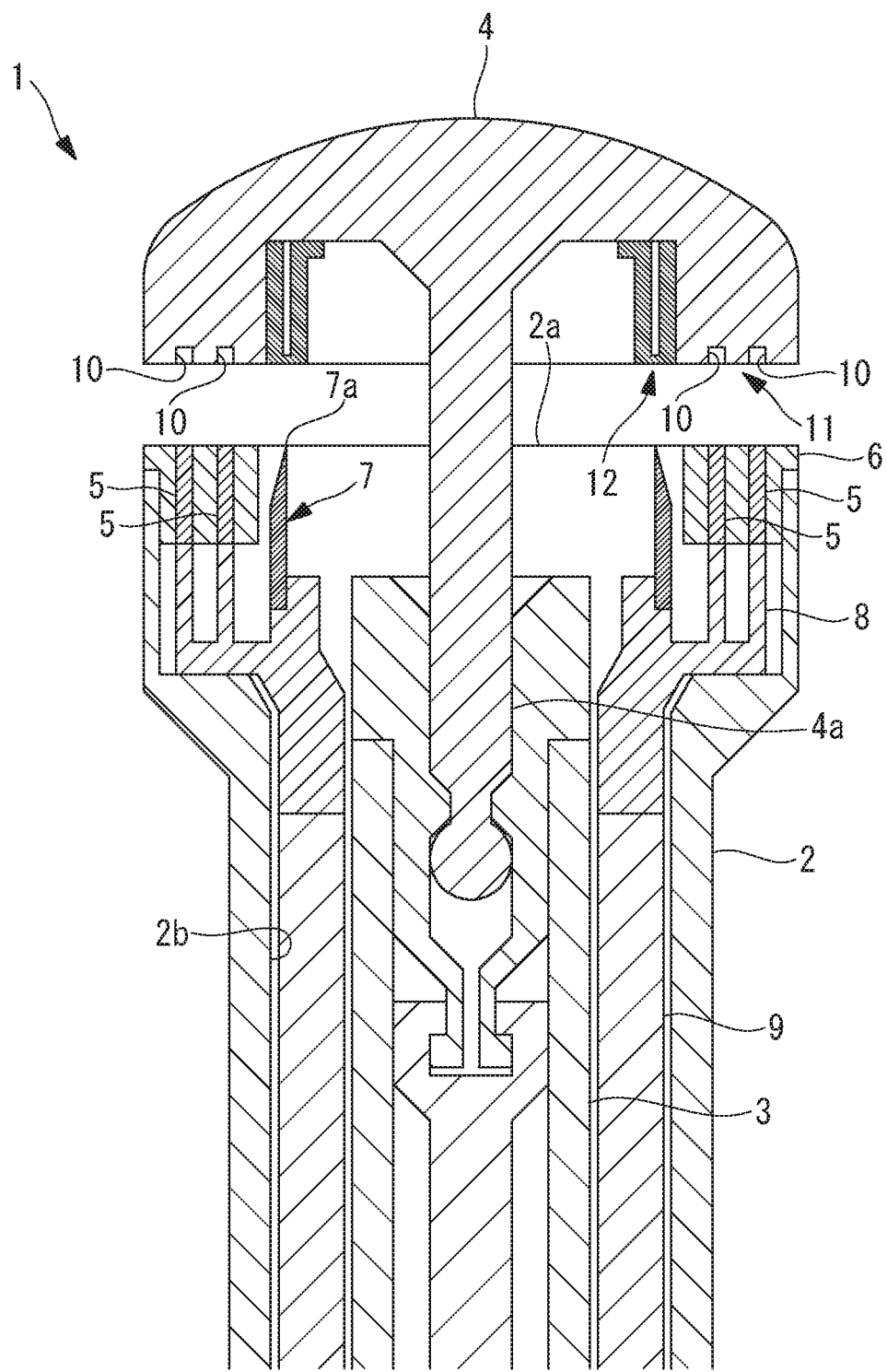
FIG. 1 is a longitudinal cross-sectional view showing a medical stapler according to an embodiment of the present invention.

As shown in FIG. 1, the medical stapler 1 according to this embodiment is a circular-type medical stapler provided with: a cylindrical staple housing 2 having a ring-shaped distal-end surface (gripping surface) 2a; a center shaft 3 that is disposed in an axial direction by passing through the same center axis as that of a center hole 2b of the staple housing 2; and an anvil 4 provided with a center rod 4a that is attached, in an attachable/detachable manner, to a distal end of the center shaft 3. By engaging the center rod 4a of the anvil 4 with the center shaft 3 and by pulling the center shaft 3 toward a base end, it is possible to dispose the anvil 4 in a closed state in which the anvil 4 is brought close to the distal-end surface 2a of the staple housing 2.

The staple housing 2 is provided with: a ring-shaped staple cassette 6 that accommodates numerous staples 5, for example, over the entire circumference thereof by arraying two rows of the staples 5 in a circumferential direction; a ring-shaped cutter 7 that is disposed radially inside over the entire circumference of the staple cassette 6; a pusher 8 that ejects, all at once, the staples 5 accommodated in the staple cassette 6 toward the anvil 4 from the distal-end surface 2a and that also supports the cutter 7; and a driving member 9 that pushes out the pusher 8.

The anvil 4 is provided with: a ring-shaped anvil portion 11 provided with a plurality of anvil pockets 10 disposed at positions facing the directions in which the individual staples 5 in the staple housing 2 are ejected (axial directions); and a receiving member 12 that is disposed radially inside the anvil portion 11 at a position facing, in the axial direction, a cutting edge 7a of the cutter 7 provided in the staple housing 2.

Figure 2:
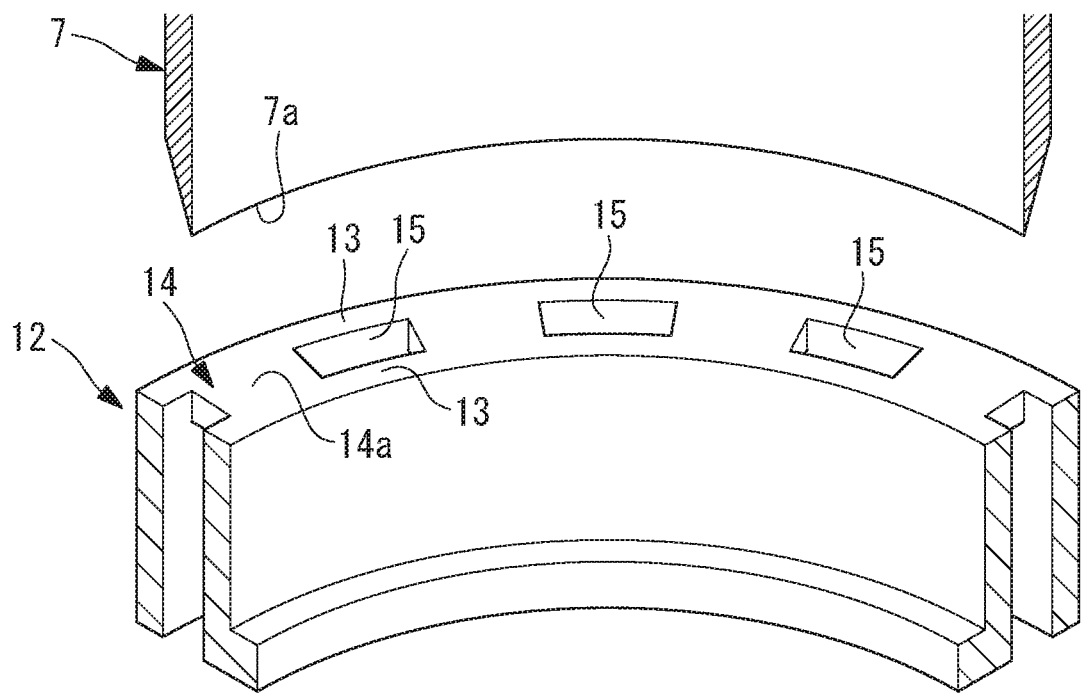
FIG. 2 is a perspective view partially showing a cutter and a receiving member provided in the medical stapler in FIG. 1.
Figure 3:
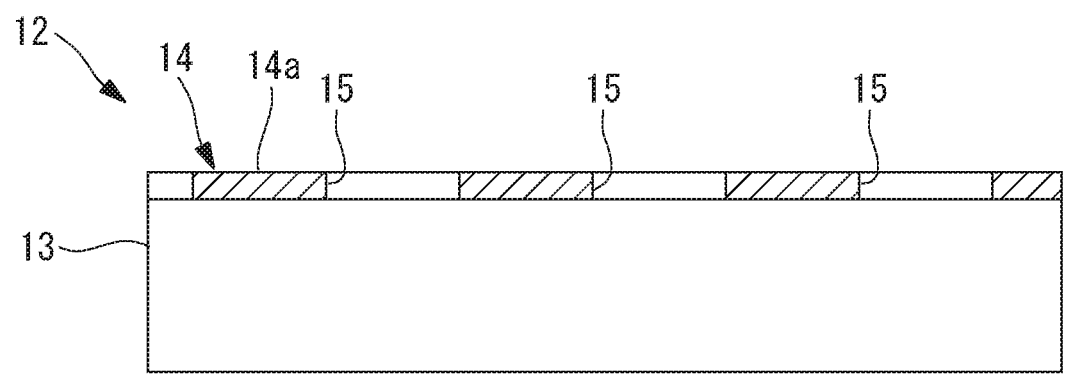
FIG. 3 is a longitudinal cross-sectional view of the receiving member in FIG. 2.

In the medical stapler 1 according to this embodiment, as shown in FIG. 2, the receiving member 12 has a substantially U-shaped lateral cross-sectional shape including two cylindrical support portions 13 that are concentrically disposed with a spacing therebetween in a radial direction, and a top plate portion (receiving surface) 14 that joins the support portions 13, in a radial direction, with each other at ends thereof on the same side in the axial direction, and, as shown in FIGS. 2 and 3, the receiving member 12 has a shape in which a plurality of holes (hole portions) 15 that pass through the top plate portion 14 in the plate-thickness direction are provided. The two support portions 13 are disposed with a spacing therebetween that allows the cutter 7 to be inserted thereinto.

As shown in FIG. 2, the plurality of holes 15 provided in the top plate portion 14 are arrayed in the circumferential direction with spacings therebetween at positions that coincide in the radial direction with the cutting edge 7a of the cutter 7 when the cutter 7 provided in the staple housing 2 is made to protrude from the distal-end surface 2a by the pusher 8, thus causing the cutting edge 7a of the cutter 7 to abut against a surface (first contact surface portion) 14a of the top plate portion 14.

The operation of the thus-configured medical stapler 1 according to this embodiment will be described below.

In order to suture and cut tissue by using the medical stapler 1 according to this embodiment, first, the anvil 4 is inserted into one of pieces of tubular tissue to be sutured such that the tubular tissue encases the anvil 4 toward the center rod 4a. The staple housing 2 is inserted into the other piece of the tubular tissue to be sutured such that the tubular tissue encases the staple housing 2 toward the center shaft 3. By doing so, the one piece of the tubular tissue is disposed so as to cover the anvil portion 11 and receiving member 12 of the anvil 4, and the other piece of the tubular tissue is disposed so as to cover the distal-end surface 2a of the staple housing 2.

In this state, by mounting the center rod 4a of the anvil 4 to the center shaft 3 of the staple housing 2 and by pulling the center shaft 3 toward the base end, the anvil 4 is brought close to the staple housing 2, thus achieving the closed state. By doing so, the tissue is sandwiched between the staple housing 2 and the anvil 4.

Then, the pusher 8 is moved toward the distal end by pushing out the driving member 9 toward the distal end, thereby ejecting, all at once, the numerous staples 5 accommodated in the staple cassette 6 by using the pusher 8, and thus, the staples 5 pass through the tissue with cutting edges thereof.

The staples 5 that have passed through the tissue are deformed by being bent by the anvil pockets 10 provided in the anvil 4, and thus, it is possible to suture the tissue by folding back needle tips of the staples 5.

By moving the pusher 8, the cutter 7 secured to the pusher 8 is also moved toward the distal end, at the moment at which the staples 5 pass through the tissue, the tissue is sandwiched between the cutting edge 7a of the cutter 7 and the top plate portion 14 of the receiving member 12 provided in the anvil 4, and, at the moment at which the suturing of the tissue with the staples 5 is completed, the cutter 7 has been advanced to a position at which the top plate portion 14 is broken. By doing so, the tissue is circularly cut by the cutter 7 radially inside the portion sutured with the staples 5. Through such motions, tubular tissue is simultaneously sutured and dissected.

In this case, although the cutter 7 cuts the tissue over the entire circumference all at once, the length by which the tissue is sandwiched between the cutter 7 and the top plate portion 14 becomes less than the entire circumferential length of the cutting edge 7a of the cutter 7 due to the holes 15 provided in the top plate portion 14 of the receiving member 12.

Specifically, at the individual time points during a cutting step in which the cutter is made to protrude toward the anvil 4 by the pusher 8, the cutting edge 7a of the cutter 7 comes into contact with only a portion of the top plate portion 14 of the receiving member 12.

Comparing this with a case in which, as in the related art, the holes 15 are not provided in the top plate portion 14 of the receiving member 12 (the cutting edge 7a of the cutter 7 and the receiving member 12 have the same overall circumferential length), because a reaction force from the receiving member 12 received by the cutter 7 is reduced, it is possible to reduce the amount of force for cutting the tissue. As a result, it is possible to reduce the burden on an operator when cutting the tissue.

Note that, although it is possible to more reliably cut the tissue by employing a sharp cutting edge in the cutter and by making the spacing between the receiving member and the support portions as small as possible, with a circular-type stapler, it is difficult to provide a sharp cutting edge in a ring-shaped cutter, and there is a limit to the sharpness enhancement of the cutting edge. In consideration of warping of the ring-shaped cutter in the circumferential direction, the combining precision between the anvil portion and the cutter, etc., there is also a limit to the size reduction of the spacing between the support portions for allowing the cutter to escape.

In contrast, with the medical stapler 1 according to this embodiment, there is an advantage in that, with a simple structure in which the holes 15 are simply provided in the top plate portion 14, it is possible to more reliably cut the tissue while reducing the amount of cutting force.

Although the effect of reducing the amount of force increases with an increase in the total length of the holes 15 in the circumferential direction with respect to the length of the top plate portion 14 in the circumferential direction, the likelihood that the tissue escapes into the holes 15 increases with an increase in the lengths of the individual holes 15, thus making it difficult to cut the tissue. Therefore, in order to reliably cut the tissue while reducing the level of cutting force, it is preferable that holes 15 having small lengths in the circumferential direction be numerously arrayed with spacings therebetween in the circumferential direction. In this embodiment, for example, a length corresponding to a half the total circumferential length is allocated to the lengths of the holes 15, and the holes 15 are arrayed within a range that is less than 30° with reference to the center axis.

Figure 4:
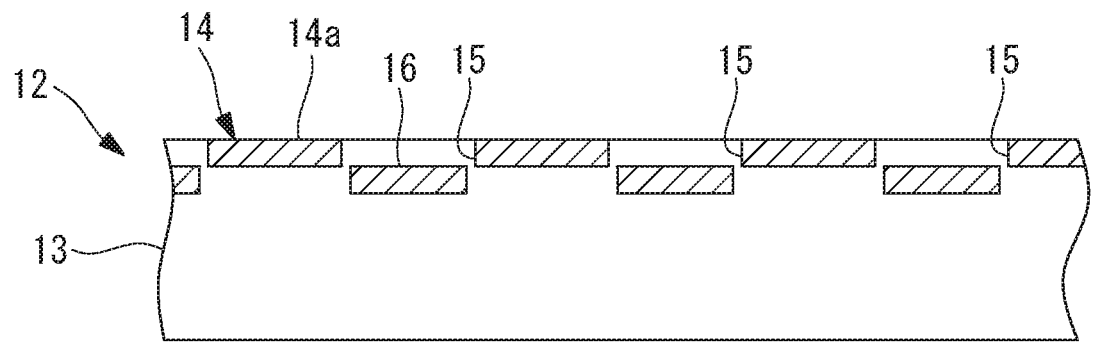
FIG. 4 is a longitudinal cross-sectional view showing a modification of the receiving member in FIG. 2.
Figure 5:
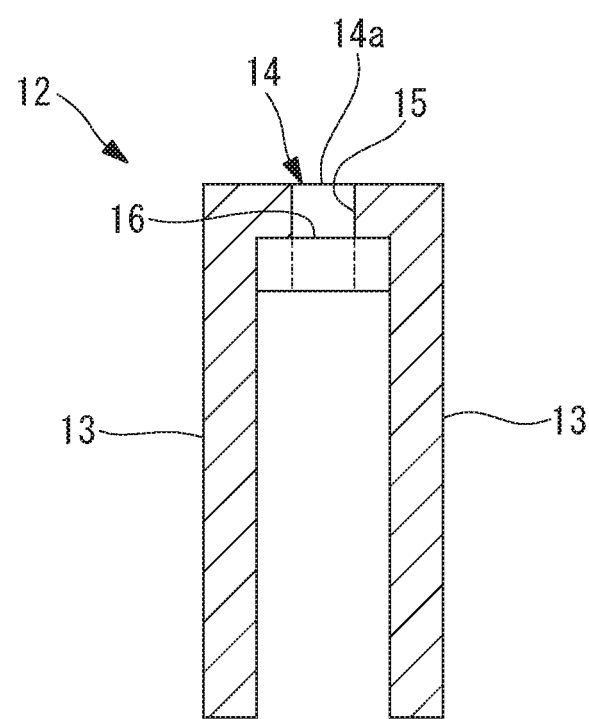
FIG. 5 is a lateral cross-sectional view showing the receiving member in FIG. 4.

As shown in FIGS. 4 and 5, this embodiment may be provided, at positions at which the holes 15 provided in the top plate portion 14 are partially closed up, with intermediate plate portions (second contact surface portions) 16 that are disposed at positions that are one step lower than the surface 14a of the top plate portion 14.

By doing so, even in the case in which portions of the tissue other than the portion thereof that is cut by being sandwiched between the top plate portion 14 and the cutting edge 7a of the cutter 7 escape into the holes 15 provided in the top plate portion 14, the portions of the tissue that have escaped into the holes 15 are sandwiched between the intermediate plate portions 16, which are disposed at the positions that are one step lower, and the cutting edge 7a of the cutter 7, and thus, it is possible to more reliably cut the tissue.

In this case, it is preferable that the size of the step difference between the top plate portion 14 and the intermediate plate portions 16 be large enough to allow the cutting edge 7a of the cutter 7 to reach the intermediate plate portions 16 after the top plate portion 14 is broken by the cutting edge 7a of the cutter 7. The receiving member 12 is formed of an ABS resin or a PE resin, and, when a load is exerted thereon by the cutter 7, as shown in FIG. 6, a slight deflection occurs before being broken.

By providing a large enough step difference such that the cutting edge 7a of the cutter 7 reaches the intermediate plate portions 16 after the top plate portion 14 is broken, the intermediate plate portions 16 would not be pressed in a state in which the cutting edge 7a of the cutter 7 is pressing the top plate portion 14. In other words, by avoiding a situation in which the top plate portion 14 and the intermediate plate portions 16 are simultaneously pressed by the cutting edge 7a of the cutter 7 in the individual time points during the cutting step, because the tissue is not simultaneously cut over the entire circumference, there is an advantage in that it is possible to more reliably reduce the level of cutting force.

Figure 6:
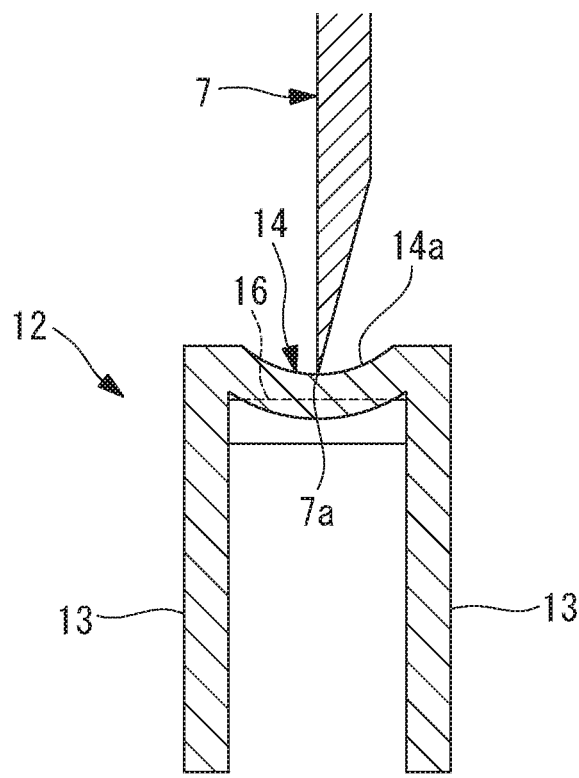
FIG. 6 is a lateral cross-sectional view showing a state in which a top plate portion of the receiving member in FIG. 4 is pressed down by a cutting edge of a cutter.
Figure 7:
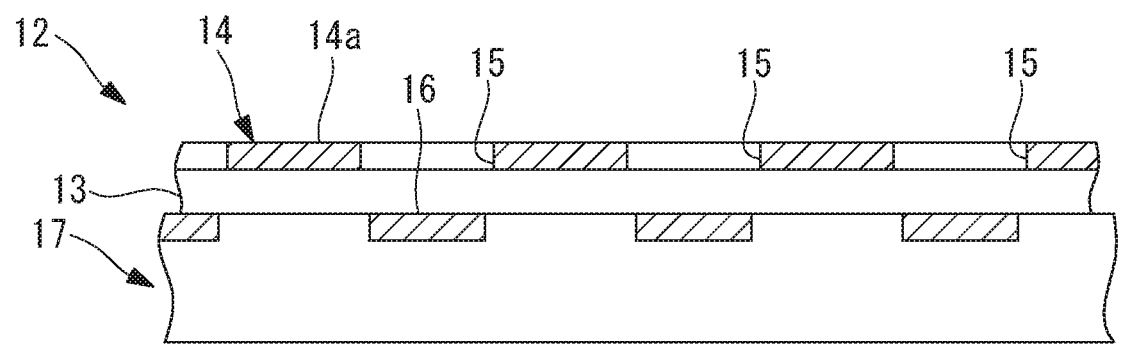
FIG. 7 is a longitudinal cross-sectional view showing another modification of the receiving member in FIG. 2.
Figure 8:
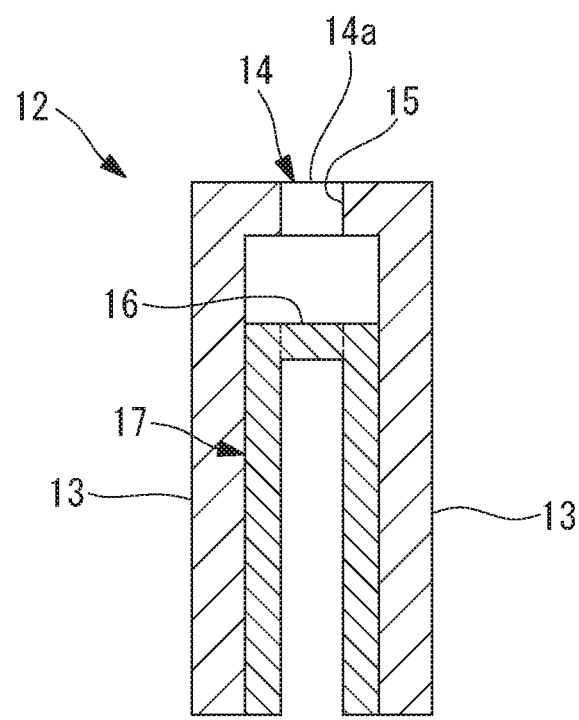
FIG. 8 is a lateral cross-sectional view showing the receiving member in FIG. 7.

Regarding the intermediate plate portions 16, as shown in FIGS. 4 to 6, the intermediate plate portions 16 may be integrally molded between the two support portions 13, or, as shown in FIGS. 7 and 8, the intermediate plate portions 16 may be configured by combining two separate receiving members 17.

Figure 9:
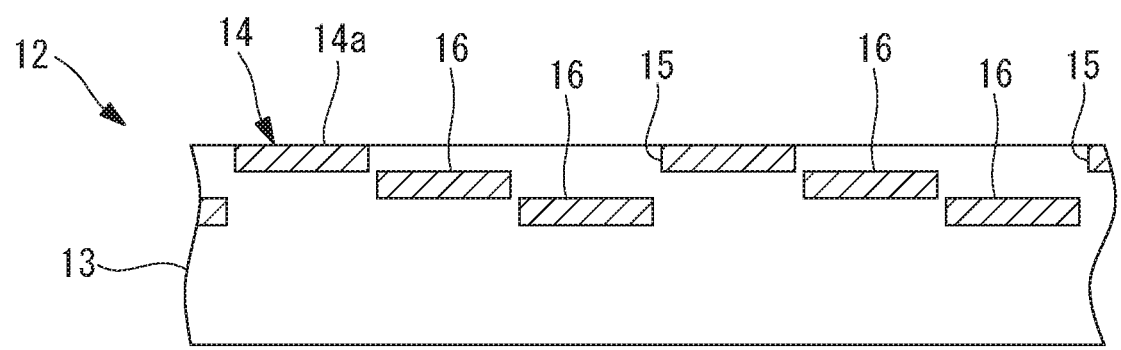
FIG. 9 is a longitudinal cross-sectional view showing another modification of the receiving member in FIG. 2.

The intermediate plate portions 16 are not limited to those provided at positions that are one step lower with respect to the top plate portion 14, and, as shown in FIG. 9, intermediate plate portions 16 having two or more steps differing in the sizes of the step difference may be provided.

By doing so, it is possible to disperse, in accordance with the number of steps, the timings at which the tissue is sandwiched between the cutting edge 7a of the cutter 7 and the top plate portion 14 or the intermediate plate portions 16, and thus, it is possible to further reduce the level of cutting force.

Figure 10:
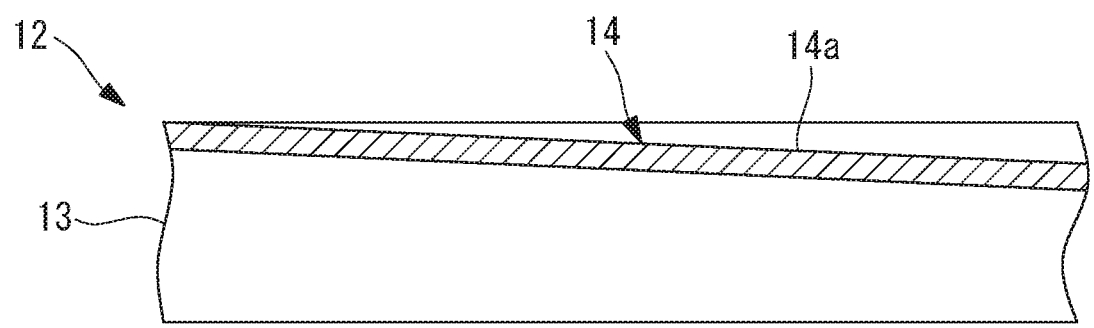
FIG. 10 is a longitudinal cross-sectional view showing another modification of the receiving member in FIG. 2.
Figure 11:
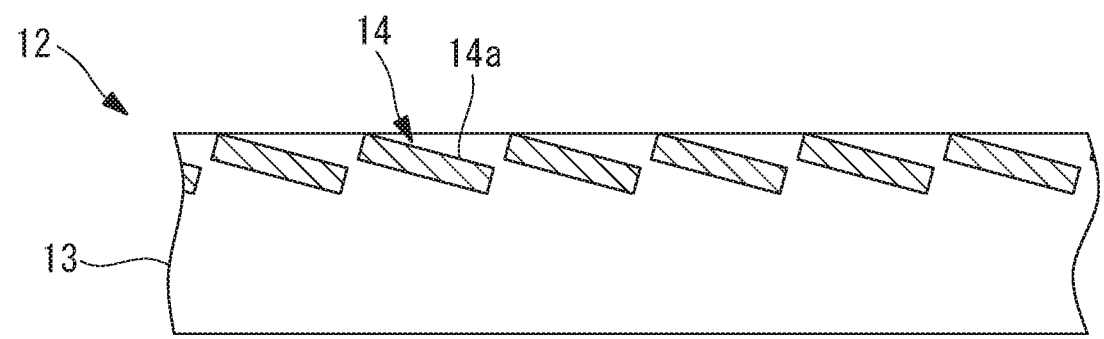
FIG. 11 is a longitudinal cross-sectional view showing another modification of the receiving member in FIG. 2.

Instead of preventing the cutting edge 7a of the cutter 7 from simultaneously coming into contact with all portions of the top plate portion 14 by providing the holes 15 in the top plate portion 14, as shown in FIGS. 10 and 11, by inclining the top plate portion 14 with respect to the cutting edge 7a of the cutter 7, a structure in which the top plate portion 14 and the cutting edge 7a of the cutter 7 do not simultaneously come into contact with each other at the individual time points during the cutting step may be employed.

By doing so, because the tissue is sequentially cut between the cutting edge 7a of the cutter 7 and the inclined top plate portion 14, it is possible to considerably reduce the level of cutting force that is exerted at a time, as compared with the case in which the cutting edge 7a of the cutter 7 and the top plate portion 14 are parallel to each other.

By employing the configuration in FIG. 11, because the load from the cutting edge 7a of the cutter 7 evenly acts over the entire receiving member 12, there is an advantage in that, by preventing the tissue from escaping along the slope, it is possible to cut the tissue without forcedly exerting a tensile force on the tissue.

In this embodiment, although the circular-type medical stapler 1 has been described as an example, alternatively, a linear-type medical stapler may be employed.

REFERENCE SIGNS LIST 1 medical stapler
2 staple housing
2a distal-end surface (gripping surface)
4 anvil
5 staple
7 cutter
7a cutting edge
12 receiving member
14 top plate portion (receiving surface)
14a surface (first contact surface portion)
15 hole (hole portion)
16 intermediate plate portion (second contact surface portion)

The invention claimed is:

1. A medical stapler comprising:
a staple housing provided with a gripping surface from which a staple for suturing tissue is ejected, the staple housing having a cutter that cuts the tissue by being made to protrude from the gripping surface;
an anvil disposed facing a direction in which the staple is ejected, the anvil being configured so that the tissue is gripped between the gripping surface and the anvil; and
a receiving member provided in the anvil, the receiving member having a receiving surface that receives a cutting edge of the cutter,
wherein the receiving surface of the receiving member has a shape in which only a portion thereof comes into contact with the cutting edge of the cutter when the cutting edge is moved to contact the receiving surface over an entire length of a cut length of the tissue; and
the shape of the receiving surface comprises, in a direction along the cutting edge of the cutter, a first contact surface that simultaneously comes into contact with the cutting edge of the cutter, and a hole provided in the first contact surface, the hole corresponding to a portion of the cutting edge extending across the hole.

2. The medical stapler according to claim 1, wherein the hole comprises a plurality of holes disposed with a spacing therebetween in the direction along the cutting edge of the cutter.

3. The medical stapler according to claim 1, further comprising:
a second contact surface that closes up at least a portion of the hole and that is disposed at a position that is depressed one step from the first contact surface.

4. The medical stapler according to claim 3, wherein a distance between the first contact surface and the second contact surface is set so as to be equal to or greater than an amount of deformation required to break the first contact surface by the cutter.

5. The medical stapler according to claim 1, wherein the receiving surface is inclined with respect to the cutting edge of the cutter.

* * * * *